(12) United States Patent
Carpenter (10) Patent No.: US 8,657,794 B2
(45) Date of Patent: Feb. 25, 2014

(54) HIGH FLOW VOLUME NASAL IRRIGATION DEVICE AND METHOD FOR ALTERNATING PULSATILE AND CONTINUOUS FLUID FLOW

(75) Inventor: Mark Carpenter, White Lake, MI (US)

(73) Assignee: Skylab Development, Inc., White Lake, MI (US)

( * ) Notice: Subject to any disclaimer, the term of this patent is extended or adjusted under 35 U.S.C. 154(b) by 602 days.

(21) Appl. No.: 12/900,792

(22) Filed: Oct. 8, 2010

(65) Prior Publication Data

US 2011/0087174 A1    Apr. 14, 2011

Related U.S. Application Data

(60) Provisional application No. 61/278,455, filed on Oct. 8, 2009.

(51) Int. Cl.
| | | |
|---|---|---|
| *A61M 31/00* | (2006.01) | |
| *B65D 37/00* | (2006.01) | |
| *B65D 5/72* | (2006.01) | |
| *B65D 25/40* | (2006.01) | |
| *B65D 35/38* | (2006.01) | |

(52) U.S. Cl.
USPC .................... 604/275; 222/213; 222/492

(58) Field of Classification Search
USPC ......... 604/212, 275, 36, 37, 48, 70, 73, 118, 604/132, 153, 185, 215, 217, 247; 222/206, 222/207, 212, 213, 491, 492; 239/101, 239/102.1

See application file for complete search history.

(56) References Cited

U.S. PATENT DOCUMENTS

| | | | | |
|---|---|---|---|---|
| 1,655,678 A | | 1/1928 | Dorment | |
| 2,135,052 A | * | 11/1938 | Rose | 604/24 |
| 2,483,661 A | * | 10/1949 | Neas | 222/4 |
| 2,564,400 A | * | 8/1951 | Hall | 128/200.14 |
| 2,571,321 A | | 10/1951 | Morris | |
| 2,577,321 A | | 12/1951 | Filger | |
| 2,578,864 A | | 12/1951 | Tupper | |
| 2,590,215 A | * | 3/1952 | Sausa | 138/45 |
| 2,672,141 A | | 3/1954 | Filger | |
| 3,176,883 A | | 4/1965 | Davis | |
| 3,211,349 A | * | 10/1965 | Prussin et al. | 222/402.18 |
| 3,221,945 A | | 12/1965 | Davis | |
| 3,330,446 A | * | 7/1967 | Grussen et al. | 222/213 |
| 3,469,582 A | * | 9/1969 | Jackson | 604/119 |
| 3,679,137 A | * | 7/1972 | Marchant | 239/327 |
| 3,883,074 A | * | 5/1975 | Lambert | 239/101 |
| 4,014,468 A | * | 3/1977 | Silverman et al. | 239/327 |
| 4,091,966 A | * | 5/1978 | Laauwe | 222/211 |

(Continued)

*Primary Examiner* — Kevin C Sirmons
*Assistant Examiner* — Andrew Gilbert
(74) *Attorney, Agent, or Firm* — Lyman Moulton, Esq.

(57) ABSTRACT

A high flow volume nasal irrigation device includes a squeeze bottle, a reservoir of liquid and a volume of air. The bottle is configured to elastically deform in response to a manual pressure from a user and thus pressurize the liquid and air. The device also includes a dip tube configured to convey a pressurized liquid flow from a first end inside the bottle to a second outside end at a lower pressure. A removable nipple cap comprises an orifice and a coaxially aligned extension configured to seal with the dip tube and to form a conduit with the tube. At least one air metering orifice is formed in the fluid conduit accessible to the to volume of air. The air metering orifice is configured to introduce a plurality of air pockets from the air volume into the liquid flow and thus generate a pulsatile fluid flow in the conduit.

6 Claims, 6 Drawing Sheets

(56) References Cited

U.S. PATENT DOCUMENTS

| | | | |
|---|---|---|---|
| 4,415,122 A * | 11/1983 | Laauwe | 239/327 |
| 4,417,861 A * | 11/1983 | Tolbert | 417/315 |
| 4,489,750 A * | 12/1984 | Nehring | 137/496 |
| 4,642,833 A * | 2/1987 | Stoltz et al. | 15/1.7 |
| 4,711,378 A * | 12/1987 | Anderson | 222/499 |
| 5,301,846 A | 4/1994 | Schmitz | |
| 5,381,961 A * | 1/1995 | Evans et al. | 239/333 |
| 5,819,801 A * | 10/1998 | Palffy | 137/826 |
| 5,899,878 A * | 5/1999 | Glassman | 604/48 |
| 6,125,843 A * | 10/2000 | Gold et al. | 128/200.23 |
| 6,669,059 B2 * | 12/2003 | Mehta | 222/211 |
| 7,097,071 B2 * | 8/2006 | Anderson et al. | 222/1 |
| 7,976,529 B2 * | 7/2011 | Carpenter | 604/516 |
| 8,366,681 B2 * | 2/2013 | Carpenter | 604/212 |
| 8,409,152 B2 * | 4/2013 | Hair | 604/275 |
| 2003/0075554 A1 * | 4/2003 | Duqueroie | 222/1 |
| 2004/0073178 A1 * | 4/2004 | Anderson et al. | 604/275 |
| 2005/0056660 A1 * | 3/2005 | Anderson et al. | 222/1 |
| 2007/0299396 A1 * | 12/2007 | Rocklin | 604/131 |
| 2011/0087174 A1 * | 4/2011 | Carpenter | 604/257 |
| 2011/0087188 A1 * | 4/2011 | Carpenter | 604/500 |

* cited by examiner

HIGH FLOW VOLUME NASAL IRRIGATION DEVICE AND METHOD FOR ALTERNATING PULSATILE AND CONTINUOUS FLUID FLOW

CROSS-REFERENCE TO RELATED APPLICATION

This application claims the benefit of the priority date of earlier filed U.S. Provisional Patent Application Ser. No. 61/278,455, filed Oct. 8, 2009 incorporated herein by reference in its entirety.

BACKGROUND

Flood irrigation differs significantly from the practice of inhaling an atomized mist into the nose. During flood irrigation, the vast majority (>95%) of fluid taken in is expelled immediately (or shortly thereafter) after the contaminants have been rinsed out. Rinsing with flood irrigation is commonly performed by ingesting the liquid solution into one nostril and concurrently expelling the solution from the other nostril. Alternately, flood irrigation is sometimes performed by ingesting the liquid solution into both nostrils simultaneously and having the excess flow to the mouth. Flood irrigation has been demonstrated to be more effective than mist for the distribution of medications and the physical rinsing of the mucus membranes of the nose and sinuses. A user of nasal flood irrigation may typically use the technique once or twice per day as opposed to a user applying a mist several to many times a day.

The use of flood irrigation to cleanse, soothe and rehabilitate nasal and sinus passages has a long history which probably began with the practice of intentional inhalation of sea water from cupped hands. Later devices such as the Neti Pot made the practice more practical. Today there is a wide array of devices and technologies to facilitate the rinsing by flood irrigation of the nasal passages and sinus cavities. Investigation of prior art shows that the number of relevant devices and techniques has grown at an increasing rate in recent decades and in particular during the last ten years. This growth in technology has paralleled the increasing popularity of the practice as the technology has become more effective and as the benefits of the practice have become more appreciated.

Within the field of flood irrigation for nasal rinsing there are developments in the liquid solutions being used and there are developments in the device which delivers the liquid stream. The liquid delivery devices for nasal flood irrigation may be generally divided into two major commercial categories—a) simple devices which dispense a continuous low pressure stream of fluid from a squeeze bottle, deformable bulb, bellows container, shower head connection, gravity feed, etc., and b) devices which use a motorized pump or other complex and expensive electromechanical apparatus to provide a pulsating stream of fluid. Both categories of device have advantages and disadvantages.

The devices which dispense a continuous low pressure stream of irrigant typically are very low in cost and may have advantageously high flow rate capability. Unfortunately, these devices offer a less than optimal cleaning ability due to the tendency of the continuous stream to form laminar flow paths across the surfaces to be rinsed and due to the surfaces not being deformed and agitated by the smooth flow stream. These continuous stream devices are also ineffectual in projecting liquid medications or irrigants into sinus cavities because the closed end cavities require time varying pressures to cause fluid entry. They also fail to rehabilitate nasal cilia which have lost motility.

The pulsating electromechanical devices have the advantages of causing a much more turbulent scouring flow with high shear stress gradients along the surfaces, causing a mixing action to reduce surface based concentration gradients and deformations of the surfaces being rinsed (for flexible surfaces) and healthy movement of the nasal cilia. Pulsating electromechanical devices unfortunately offer a less than optimal flow rate. Additionally, the pulsatile electromechanical devices are significantly more complex and costly, with purchase cost approximately ten times that of a squeeze bottle irrigator. This high cost prevents many potential users from purchasing them and does not favor the periodic disposal of the device which is necessary to avoid colonization by bacteria and molds.

SUMMARY OF THE INVENTION

A high flow volume nasal irrigation device for pulsatile and continuous fluid flow is disclosed. The device includes a chamber having a reservoir of liquid and a volume of air. The chamber is configured to elastically deform in response to an applied pressure and thus pressurize the liquid and air therein. The device also includes a fluid conduit configured to convey a pressurized liquid flow from a first end inside the chamber to a second end outside the chamber at a lower pressure. At least one air metering orifice is formed in the fluid conduit. The air metering orifice is configured to introduce a plurality of air pockets from the air volume into the liquid flow and thus generate a pulsatile fluid flow in the conduit.

A disclosed high flow volume nasal irrigation device allows a user to alternate pulsatile and continuous fluid flow. The device may also include a squeeze bottle with an open end, a reservoir of liquid and a volume of air. The squeeze bottle is configured to elastically deform in response to a manual pressure from a user and thus pressurize the liquid and air. The device also includes a dip tube configured to convey a pressurized liquid flow from a first end inside the squeeze bottle to a second end outside the squeeze bottle. The second end comprises a void in the tube wall. A removable nipple cap is also included, the cap connected to the squeeze bottle open end. The cap comprises a nipple orifice and a coaxially aligned cylindrical socket configured to rotatably seal with the dip tube second end to form a conduit with the tube. An air channel is formed axially and adjacent to the cap socket. The air channel and the second end void together are configured to form an air metering orifice when rotatably aligned to introduce a plurality of air pockets into the fluid flow from the air volume and thus generate a pulsatile fluid flow.

A high flow volume nasal irrigation device for pulsatile and continuous fluid flow may include the squeeze bottle as configured above. The device may also include a dip tube configured to convey a pressurized liquid flow from a second end outside the squeeze bottle to a first end inside the squeeze bottle configured to extend into the reservoir of liquid. The device may also include a removable cap disposed on the squeeze bottle open end. The cap comprises a nipple end and an opposing coaxial extension where the extension comprises an externally threaded channel and is configured to seal to the tube inside diameter. The nipple end of the cap comprises a tube stop and an orifice. An air metering orifice is formed at a mouth of the externally threaded channel in a hollow area above the tube stop accessible to the volume of air to introduce a plurality of air pockets into the fluid flow and thus generate a pulsatile fluid flow.

Throughout the description, similar or same reference numbers may be used to identify similar or same elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

The shear forces, momentum, and solvency of pulsatile nasal irrigation entrains mucus and contaminants and removes them from bodily cavities. Pulsatile nasal irrigation of the nose and sinus cavities with sea water, saline solution, liquid medications, and similar liquids is a way to reduce sinus irritation, congestion, and particularly the allergens that cause allergic rhinitis. Pulsatile nasal irrigation is also beneficial after certain surgical procedures, in treating sinus infections, and other medical conditions.

The present disclosure is a unique and non-obvious nasal flood irrigation device which provides superior cleaning action at a cost comparable to and competitive with the lowest cost current technology rinsing devices. The disclosed device provides: a) a liquid flow rate higher than any other known nasal irrigator, b) pulsatile irrigation when desired by the user and c) minimal cost. Higher flow rates create higher Reynolds numbers and therefore more turbulent liquid flow and better dilution and suspension of contaminants. Pulsatile irrigation divides the liquid stream into a series of individual packets of liquid which impact the surface to be cleansed with a splattering action and at a velocity greater than that expected of a continuous stream of liquid expelled under the same conditions. Cost is minimized as the device consists of a very inexpensively modified version of the least expensive of the known types of high volume nasal irrigation devices: the squeeze bottle or similar hand compressed devices.

Embodiments of the disclosed device may comprise a deformable bottle initially filled by the user to a predetermined level with the desired rinsing liquid. Above the predetermined level there is intentionally trapped a to predetermined volume of air. The bottle has at its top a cap which includes a nipple orifice at the top to seal against a nostril and a nipple extension at its bottom to attach to a pickup tube which extends to the bottom of the bottle. Therefore, the cap is also known as a nipple cap herein. An air metering orifice extends through the wall of the pickup tube near the top of the pickup tube. Through the air metering orifice, the air in the upper portion of the bottle (when held upright) is intermittently allowed to intersperse with the liquid flowing up the pickup tube. This occurs because the air is pressurized to the some pressure as the water when the sides of the bottle are deflected inward. When in operation the air alternates with the liquid within the diameter of the pickup tube above the orifice and up through the dispensing orifice. The total volume of the stream exiting the device is dependent on the diameter an internal passage or conduit comprising a pickup tube, cap, and dispensing orifice. This conduit is large enough so that the contents of the bottle may be emptied in approximately 8 seconds at normal squeeze pressure. The resulting internal passages are approximately 4.5 mm in diameter to achieve this.

During operation, the bottle is compressed to elevate the pressure of both the water and air (nearly equally) within the bottle relative to the dispensing orifice. Water from the bottom of the bottle is urged up the pickup tube by the pressure difference between the liquid intake opening at the bottom of the pickup tube and the dispensing orifice at the top of the cap.

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

Figure 1:
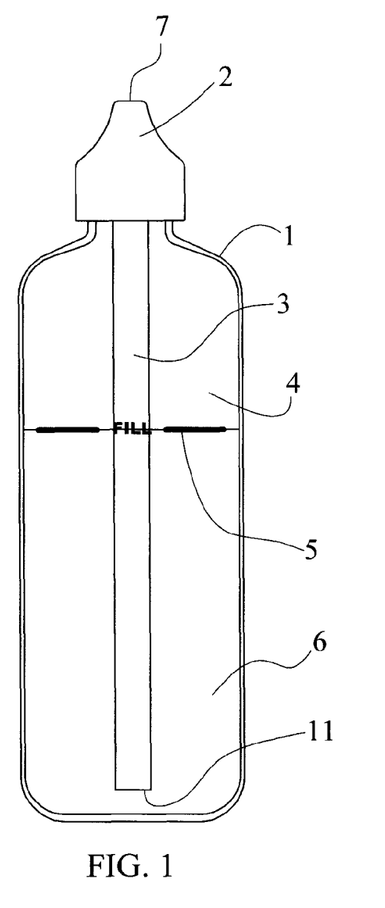
FIG. 1 is an elevational view of a high flow volume nasal irrigation device for alternating pulsatile and continuous fluid flow in accordance with an to embodiment of the present disclosure.

FIG. 1 is an elevational view of a high flow volume nasal irrigation device for alternating pulsatile and continuous fluid flow in accordance with an embodiment of the present disclosure. The device as depicted includes a chamber 1, a cap 2, a dip tube 3, a volume of air 4, a fluid line 5, a reservoir of liquid 6, a to nipple orifice 7, an air metering orifice (not shown) and a fluid intake opening 11. The chamber 1, also known as a squeeze bottle herein, is configured to elastically deform in response to an applied pressure and thus pressurize the liquid 6 and air 4 therein. The device also includes a fluid conduit comprising the dip tube 3 and the cap 2 together configured to convey a pressurized liquid flow from a first end 11 inside the chamber 1 to a second end connected to the cap 2 outside the chamber 1 at a lower pressure. An inside nominal diameter of the dip tube 3 may be 4.5 mm (0.180 inches) with a corresponding cross sectional area of 15.9 mm$^2$ (0.025 inches$^2$). An inside maximum diameter of the dip tube 3 may be 7.0 mm (0.280 inches) with a corresponding cross sectional area of 38.5 mm$^2$ (0.060 inches$^2$). An inside minimum diameter of the dip tube 3 may be 2.0 mm (0.080 inches) with a corresponding cross sectional area of 3.1 mm$^2$ (0.005 inches$^2$). The circumferential fluid line 5 and indicia placed externally on the bottle 1 indicate a minimum ratio of liquid 6 to air 4 to produce the pulsatile fluid flow in the conduit for a first squeeze of the bottle 1 by a user.

Embodiments of the present disclosure include a screw-on cap 2 with an upper surface adapted to fit sealingly against a user's nostril. The underside of the screw-on cap may engage an elastomeric pickup tube 3 through a press fit interface. The pickup tube 3 may extend nearly to the bottom of the deformable plastic bottle 1, leaving a large enough gap to the bottom of the bottle 1 so that there is no significant flow restriction through the tube 3. The bottle 1 includes a painted or inked horizontal line 5 on its exterior to indicate an initial liquid 6 level. This level is significant for two reasons: 1) the liquid solution 6 may be prepared by mixing water (or other liquid) with a pre-measured solute. In this case the line 5 serves to control the quantity of liquid 6 so that the resulting solution has the desired concentration. 2) The line 5 serves to control the ratio of the air volume 4 to the volume of the liquid solution 6. This ratio should closely correspond to the volume ratio exiting the device (which is based on the relation between the liquid flow area and an air metering orifice). In this view, a relatively large volume of air at the top of the bottle is readily apparent.

Figure 2:
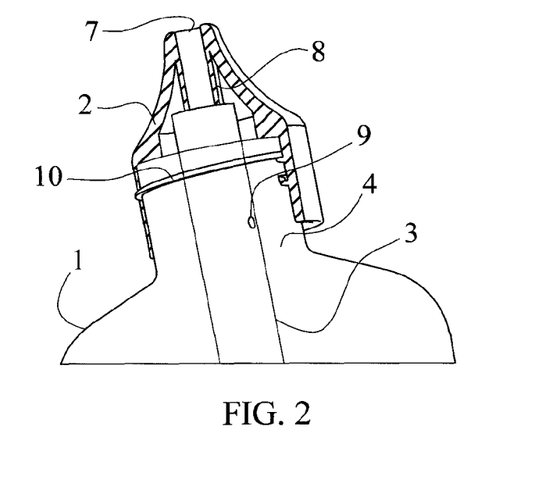
FIG. 2 is a partial sectional view through the cap of the device in accordance with an embodiment of the present disclosure.

FIG. 2 is a partial sectional view through the cap of the device in accordance with an embodiment of the present disclosure. The view includes the chamber 1, the cap 2, the dip tube 3, the volume of air 4, the nipple orifice 7, a nipple extension 8, an air metering orifice 9 and a threaded connection 10. At least one air metering orifice 9 is formed in the dip tube 3 section of the fluid conduit as shown so as to be accessible to the volume of air 4 inside the bottle 1. Less than three air metering orifices may be comprised in the dip tube and the cap. The air metering orifice 9 is therefore configured to introduce a plurality of air pockets from the air volume 4 into the liquid flow from the reservoir of liquid (not shown) and thus generate a pulsatile fluid flow in the conduit starting at the air metering orifice 9 and continuing to and out through the nipple orifice 7. The threaded connection 10 between the bottle and the cap forms a fluid tight seal to maintain the internal pressure in the bottle resulting from a user squeezing the bottle or any other action on the bottle creating pressure therein.

The disclosed device may include embodiments having a cap 2 and a dispensing orifice 7 at its top through which a fluid stream exits the device into the nostril. The cap 2 is sealingly attached to the deformable bottle 1 by a threaded connection 10 during immediate use. The position of the metering orifice 9 may be vertically located so that it will be as high as possible along the length of a pickup tube 3 to avoid the admittance of liquid when the bottle is held at an angle or moved in a manner that causes sloshing. However, the air metering orifice 9 may not be so high that its internal surface is obstructed by its attachment to the screw on cap 2 under any adverse condition of production tolerance.

Figure 3:
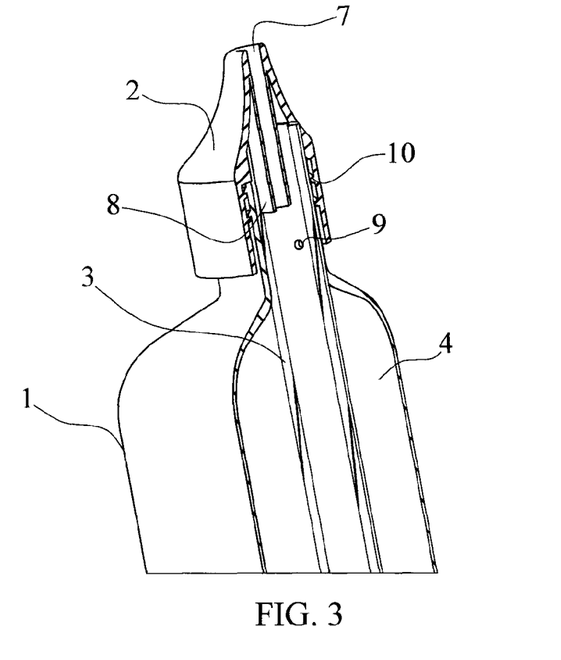
FIG. 3 is a cross-sectional view through the cap and bottle including a sectional view of the tube in accordance with an embodiment of the present disclosure.

FIG. 3 is a cross-sectional view through the cap and bottle including a sectional view of the tube in accordance with an embodiment of the present disclosure. The view therefore includes the chamber 1, the cap 2, the dip tube 3, the volume of air 4, the nipple orifice 7, the nipple extension 8, the air metering orifice 9 and the threaded connection 10. The cap includes the nipple extension 8 opposite the nipple orifice 7. The nipple extension 8 is configured to be received into and form a seal with the inside wall of the dip tube 3. An inside nominal diameter of the nipple orifice 7 may be 4.5 mm (0.180 inches) with a corresponding cross sectional area of 15.9 mm$^2$ (0.025 inches$^2$). An inside maximum diameter of the nipple orifice may be 7.0 mm (0.280 inches) with a corresponding cross sectional area of 38.5 mm$^2$ (0.060 inches$^2$). An inside minimum diameter of the nipple orifice may be 2.0 mm (0.080 inches) with a corresponding cross sectional area of 3.1 mm$^2$ (0.005 inches$^2$). The cross sectional area of the nipple extension 8 of the orifice may also be of similar diameter and area.

In embodiments, the air metering orifice 9 may be formed in a material separate from the conduit in order to more precisely control forming the air metering orifice 9 in which case the separate air metering orifice is configured to fit into the wall of the conduit within the bottle 1. The separate air metering orifice may be configured to fit into the conduit via threads, barbs, flanges and the like formed in at least one of the conduit and the separate material. Furthermore, the fluid flow conduit may comprise a plurality of air metering orifices 9 and a plurality of plugs. Each of the plugs may be configured to seal at least one of the air metering orifices 9 allowing less than the three to be open during use of the high flow volume nasal irrigator device to produce a pulsatile flow.

Additional embodiments include a nipple extension 8 protruding downward from the main body of cap 2 to sealingly connect to a pickup tube 3 by a light press fit. Thus, an air metering orifice 9 in the tube 3 provides a continuously open air passage between the upper portion of air volume 4 (within cap 2) and the interior of the pickup tube 3.

Figure 4:
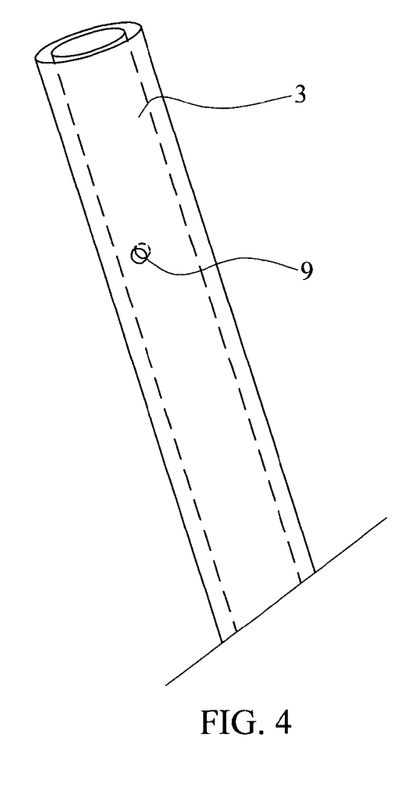
FIG. 4 is a perspective view of one end of the dip tube showing detail of an air metering orifice in accordance with an embodiment of the present disclosure.

FIG. 4 is a perspective view of one end of the dip tube showing detail of an air metering orifice in accordance with an embodiment of the present disclosure. The perspective view depicts the dip tube 3 and the air metering orifice 9. An inside nominal diameter of the air metering orifice 9 may be 1.25 mm (0.050 inches) with a corresponding cross sectional area of 1.2 mm$^2$ (0.002 inches$^2$). An inside maximum diameter of the air metering orifice 9 may be 1.8 mm (0.070 inches) with a corresponding cross sectional area of 2.5 mm$^2$ (0.004 inches$^2$). An inside minimum diameter of the air metering orifice 9 may be 1.0 mm (0.040 inches) with a corresponding cross sectional area of 0.78 mm$^2$ (0.001 inches$^2$). The air metering orifice 9 is placed proximal to the second end of the dip tube in order to be accessible to the volume of air (not shown) during a squeeze of the bottle 1. However, an alternative placement of the dip tube 3 in relation to the cap 2 and the bottle 1 (not shown) may produce differing results.

Figure 5:
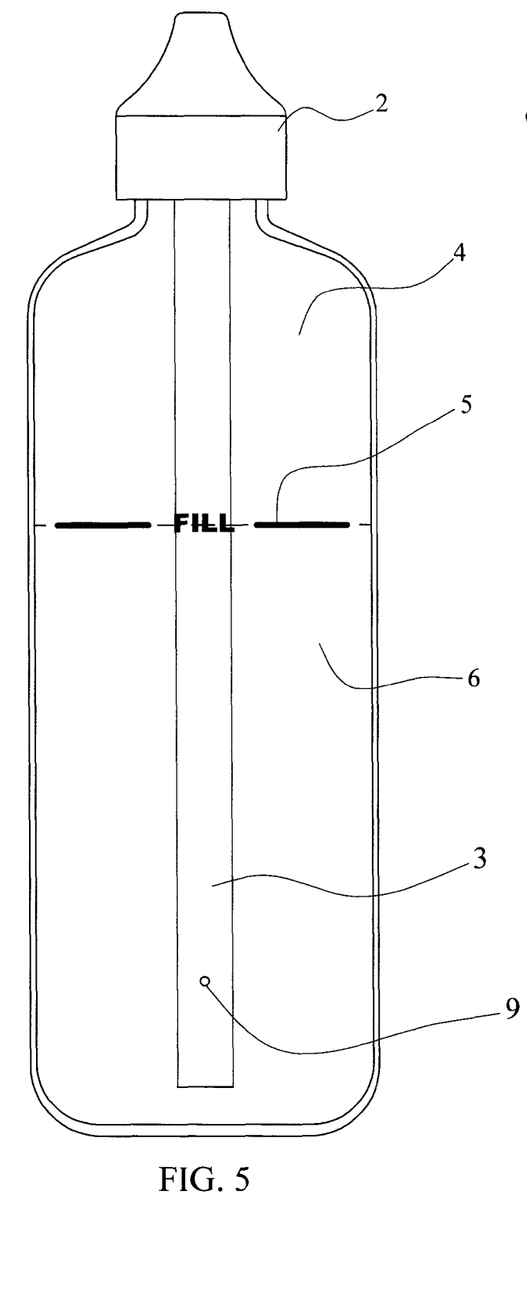
FIG. 5 is an elevational view through the bottle showing an alternate position of the dip tube configurable by a user in accordance with an embodiment of the present disclosure.

FIG. 5 is an elevational view through the bottle showing an alternate position of the dip tube configurable by a user in accordance with an embodiment of the present disclosure. The partial section includes all of the elements of FIG. 1 but depicts the dip tube 3 configured in an inverted position with respect to the cap 2. Therefore, a first end of the tube 3 connects to the cap 2 and the tube 3 second end extends into the reservoir of liquid 6. This configuration allows a user to submerge the air metering orifice 9 into the liquid 6 and allow the user of the device to produce a continuous liquid stream from the reservoir 6 uninterrupted by the introduction of air pockets from the air volume 4. However, once the liquid 6 level falls below the air metering orifice 9 the remaining liquid 6 may be unavoidably expelled in a pulsatile stream.

Figure 6:
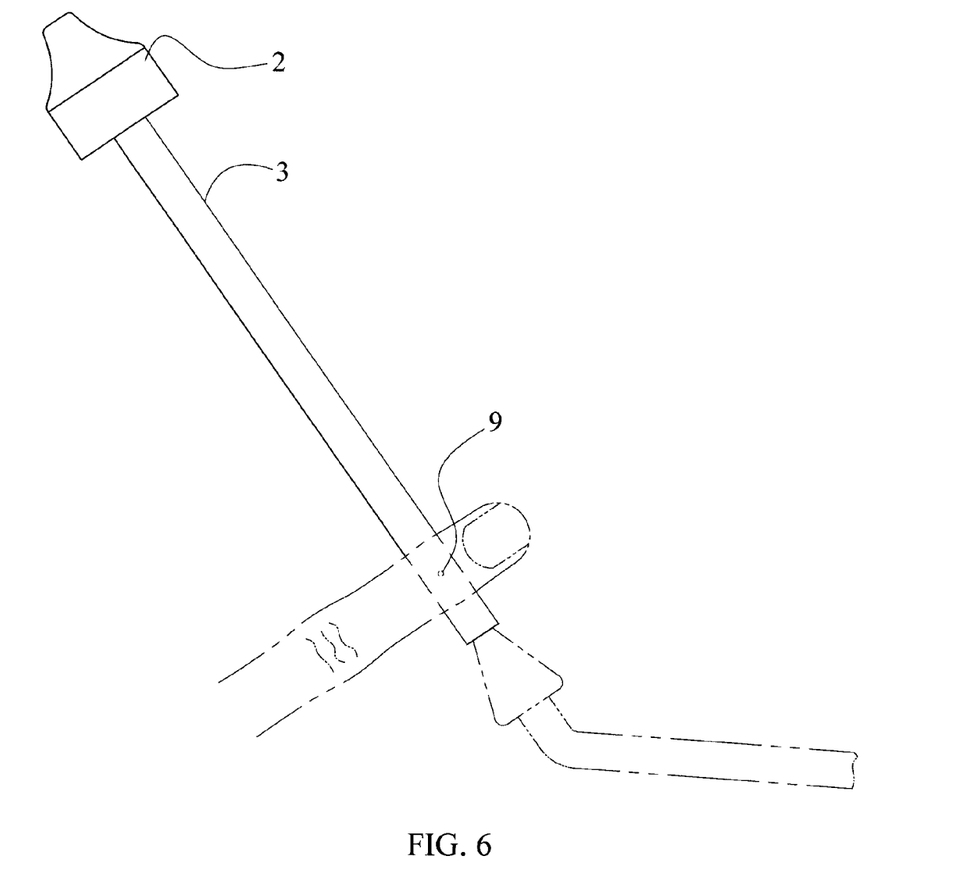
FIG. 6 is a view of the cap and dip tube configured as a nasal adapter for an external pump in accordance with an embodiment of the present disclosure.

FIG. 6 is a view of the cap and dip tube configured as a nasal adapter for an external pump in accordance with an embodiment of the present disclosure. In the embodiment depicted, the dip tube 3 and connected cap 2 are removed from the bottle 1 (not shown) and a first end of the dip tube 3 is connected to a power operated oral irrigator. A user's finger is placed over the air metering orifice 9 in order to modulate the strength of the flow stream provided to the nose by controlling the air metering orifice 9 with a finger as needed.

Figures 7, 8, 9, 10:
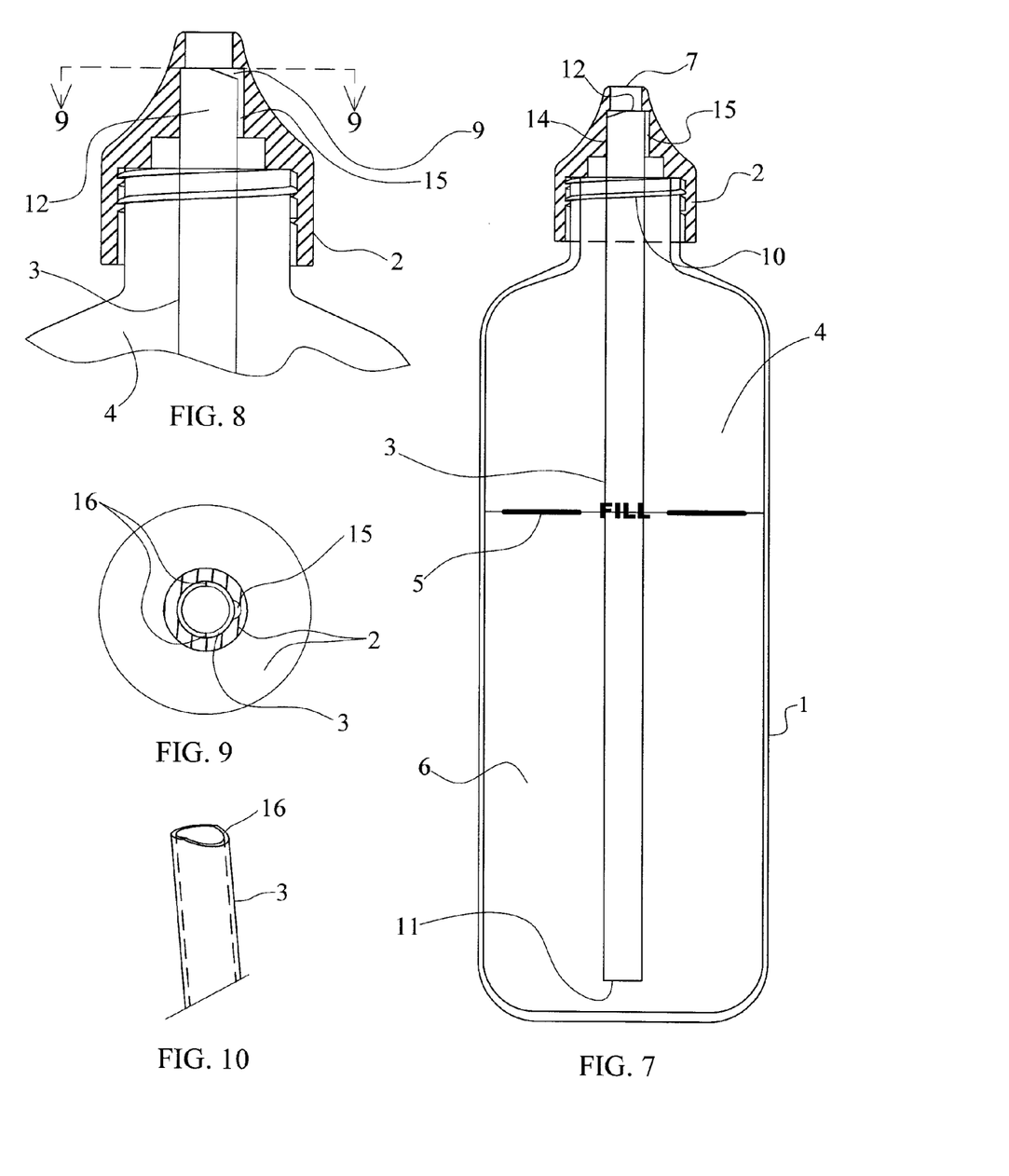
FIG. 7 is a sectional view of the device comprising a rotatable tube configured to adjust the size of an air metering orifice in conjunction with the cap in accordance with an embodiment of the present disclosure.
FIG. 8 is an enlarged view of the cap depicting the interface between the cap and the dip tube to produce a variable air metering orifice in accordance with an embodiment of the present disclosure.
FIG. 9 is a sectional view through the top diameter of the cap showing an air passage through the cross section 9-9 of FIG. 8 in accordance with an embodiment of the present disclosure.
FIG. 10 is a perspective view of the second end of the dip tube showing detail of a beveled end of the dip tube in accordance with an embodiment of the present disclosure.

FIG. 7 is a sectional view of a device comprising a rotatable tube configured to adjust the size of an air metering orifice in conjunction with the cap in accordance with an embodiment of the present disclosure. The view depicted includes the bottle 1, a cap 2, a dip tube 3, the volume of air 4, the horizontal line 5, the reservoir of liquid 6, the nipple orifice 7, the threaded connection 10, the tube first end or fluid intake opening 11, the tube second end 12 and the socket 14. The dip tube 3 thus configured conveys a pressurized liquid flow from the first end 11 inside the squeeze bottle 1 to a second end 12 outside the squeeze bottle 1. The second end comprises a void such as a gap, a notch, a bevel and any other void in the tube wall. A bevel serving as the void in the second end extends near the axial center or diameter of the tube end 12 to its circumference at an acute angle shown in detail in FIG. 10 below. The removable cap 2 disposed on the squeeze bottle 1 open end comprises the nipple orifice 7 and a coaxially aligned cylindrical socket 14 configured to rotatably seal with the dip tube 3 second and beveled end 12 to form a conduit extending from the tube 3 through the nipple orifice 7. An air channel 15 is formed in the cap 2 axially and immediately adjacent to the cap socket 14. The air channel 15 and the bevel are configured to form an effective air metering orifice when rotatably aligned to each other. The resulting air metering orifice thus in communication with the volume of air 4 may introduce a plurality of air pockets into the fluid flow and generate a pulsatile fluid flow at the nipple orifice 7. The circumferential fluid line 5 and indicia placed externally on the bottle 1 indicate a minimum ratio of liquid 6 to air 4 to produce the pulsatile fluid flow in the dip tube 3 for a first squeeze of the bottle 1 by a user.

By adjusting the size of the air metering orifice 9 relative to the diameter of the internal liquid passage the device may be tailored to give a wide range of pulsatile frequencies. Increases in the air metering orifice size may decrease the pulsatile frequency. In addition to varying the frequency the ratio of the air metering orifice 9 to the internal liquid passage may also determine the overall ratio of air to liquid that is dispensed from the dispensing or nipple orifice 7. An air metering orifice 9 which is too small may not generate pulsatile flow but may simply create bubbles in the continuous liquid stream. An air metering orifice 9 which is too large may admit so much air that cleaning action is reduced and the flow stream becomes uncomfortable to the user. Experimentation with devices having 4.5 mm diameter liquid passages have shown that the best air metering orifice 9 sizes are approximately 1.25 mm diameter with a range of 1.0 mm to 1.8 mm being judged to be acceptable. The pulsation frequency may be ~500-1000 cycles per minute under these parameters.

FIG. 8 is an enlarged view of the cap depicting the interface between the cap and the dip tube to produce a variable air metering orifice in accordance with an embodiment of the present disclosure. The view thus depicted includes all of the elements of FIG. 7 with the exception of the reservoir of liquid 6. An intentional and variable alignment of the dip tube 3 second and beveled end 12 and the air channel 15 produce variable size and variable length air pockets in the fluid flow at the discretion of the user. The user may thus 'dial in' effective air metering orifices in order to achieve a desired pulse at the nipple orifice 7. A non-alignment of the second and beveled end 12 and the air channel 15 produces a continuous fluid flow at the nipple orifice 7. The cross section given in FIG. 8 by the line 9-9 is illustrated in FIG. 9 and explained below.

FIG. 9 is a sectional view through the top diameter of the cap showing an air passage through the cross section 9-9 of FIG. 8 in accordance with an embodiment of the present disclosure. The depicted view includes both an unsectioned portion and a sectioned portion of the cap 2, the second end of the dip tube 3 and bevel 16 and the air channel 15. The tube 3 may thus be intentionally rotated within the socket 12 of the cap 2 by a user until the bevel 16 no longer aligns with or faces the air channel 15 and air flow is shut off.

FIG. 10 is a perspective view of the second end of the dip tube showing detail of a beveled end of the dip tube in accordance with an embodiment of the present disclosure. The present view details the bevel 16 starting near the diameter of the tube second end 12 to its circumference at an acute angle. The angle depicted approximates 33 degrees but larger angles may also be employed. However, the second end may also comprise a void such as a gap, a notch or any other void in the tube wall which may be used to align with the cap air channel 15 and effectuate the air metering orifice 9.

Figure 11:
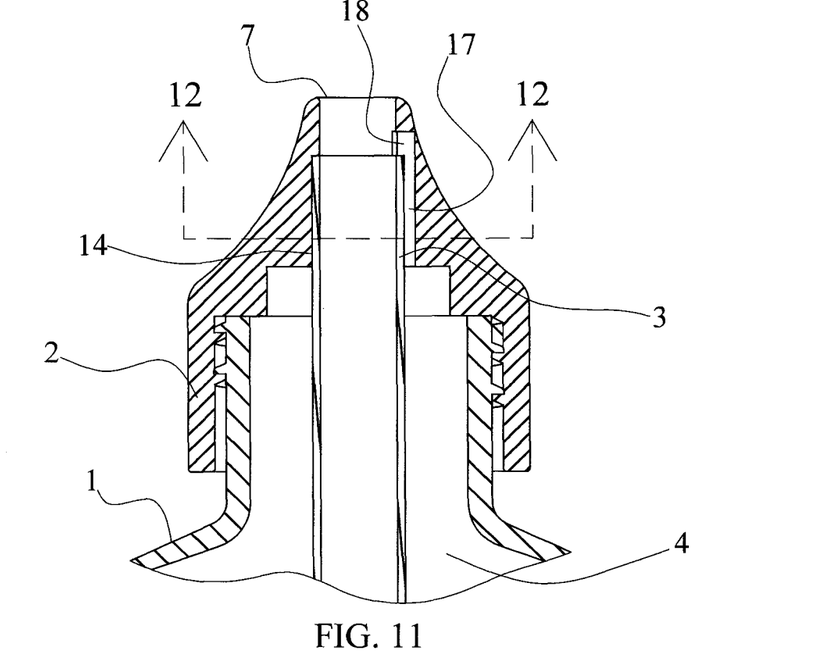
FIG. 11 is a sectional view of a dip tube and a cap comprising an air metering orifice in accordance with an embodiment of the present disclosure.

FIG. 11 is a sectional view of a dip tube and a cap comprising an air metering orifice in accordance with an embodiment of the present disclosure. The depiction includes the bottle 1, the cap 2, the dip tube 3, the volume of air 4, the nipple orifice 7, the threaded connection 10, the socket 14, an extended air channel 17 and an air metering orifice 18. The extended air channel 17 is formed axially and immediately adjacent to the cap socket 14 but further extends beyond the dip tube 3 towards the nipple orifice 7 to form a fixed air metering orifice 18 therein independent of the rotation of the dip tube 3. The cross section given in FIG. 11 by the line 12-12 is illustrated in FIG. 12 and explained below.

Figure 12:
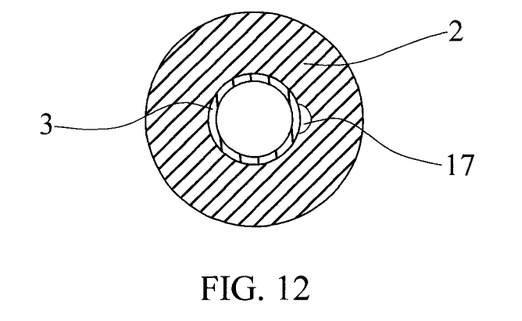
FIG. 12 is a detail of the cap, dip tube and air metering orifice through the cross section 12-12 of FIG. 11 in accordance with an embodiment of the present disclosure.

FIG. 12 is a detail of the cap, dip tube and air metering orifice through the cross section 12-12 of FIG. 11 in accordance with an embodiment of the present disclosure. The depiction includes the cap 2, the dip tube 3 and the extended air channel 17. The extended air channel 17 precludes secondary manufacturing operations to the dip tube 3 in order to produce a pulsatile fluid flow. Single extended air channel 17 and an associated single fixed air metering orifice 18 (not depicted) may be accompanied by additional multiple extended air channels and multiple fixed air metering orifices in embodiments of the disclosed device to generate further pulsatile fluid flow available to the user.

Figure 13:
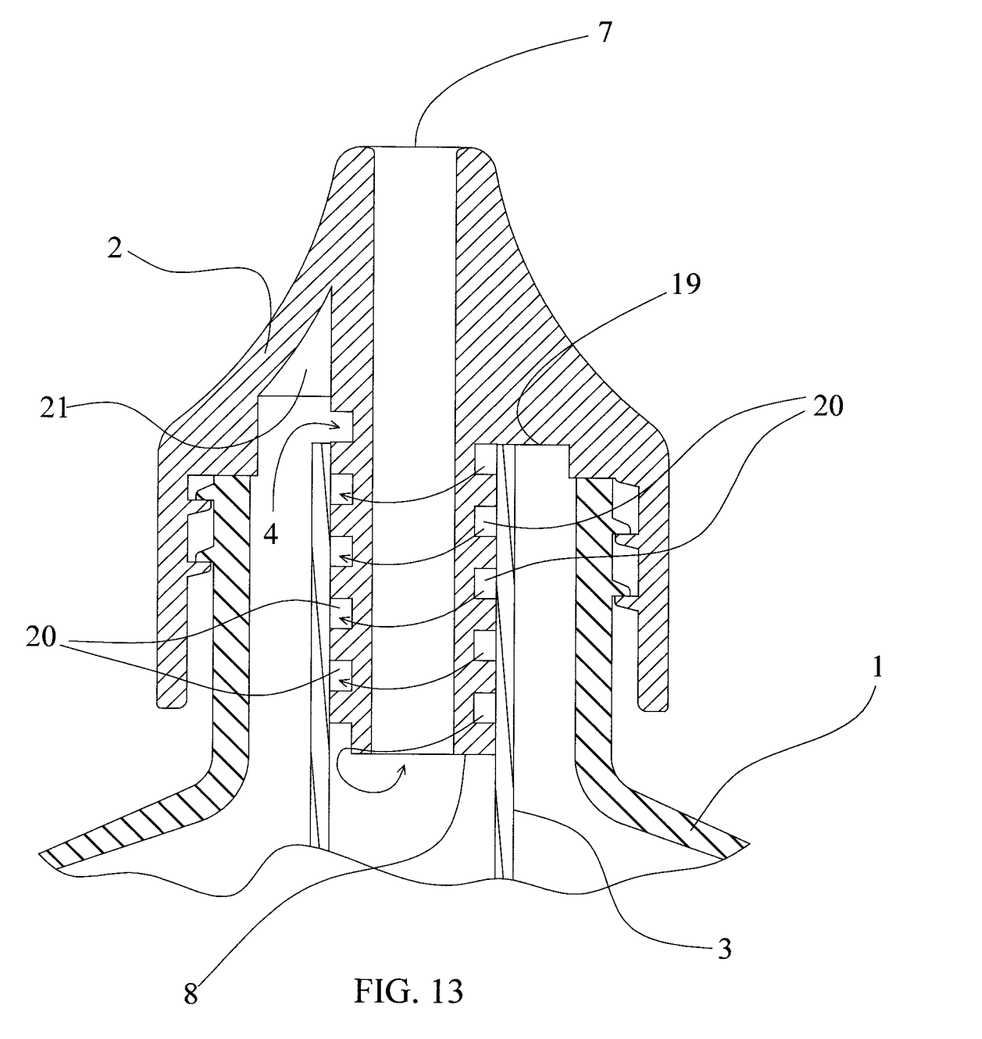
FIG. 13 is a sectional view of a high flow nasal irrigation device for to alternating pulsatile and continuous fluid flow including a threaded air channel in accordance with an embodiment of the present disclosure.

FIG. 13 is a sectional view of a high flow nasal irrigation device for alternating pulsatile and continuous fluid flow including a threaded air channel in accordance with an embodiment of the present disclosure. The depicted device includes the bottle 1, the cap 2, the dip tube 3, the volume of air 4, the nipple orifice 7, the nipple extension 8, the threaded connection 10, a tube stop 19 and an externally threaded air channel 20. The squeeze bottle 1 comprises an open end, a reservoir of liquid 6 (not shown) and the volume of air 4. The bottle 1 is configured to elastically deform in response to a manual pressure from a user and thus pressurize the liquid 6 and air 4. The dip tube 3 is configured to convey a pressurized liquid flow from a first end 11 in a reservoir of liquid 6 inside the squeeze bottle 1 to a second end 12 outside the squeeze bottle 1. The removable cap 2 is disposed on the squeeze bottle 1 open end. The cap 2 comprises a nipple orifice 7 end and an opposing coaxial nipple extension 8, where the nipple extension 8 is configured to seal to the tube 3 and comprises a threaded channel 20. The nipple orifice 7 end of the cap 2 comprises a tube stop 19 and a nipple orifice 7. An air metering orifice is formed at a mouth of the threaded channel 20 in a hollow area 21 above the tube stop 19 accessible to the volume of air 4 to introduce a plurality of air pockets into the fluid flow and thus generate a pulsatile fluid flow. A helix pitch of the threaded channel 20 may match a helix pitch of the threaded connection 10 on the cap to enable a one-piece injection mold of the cap.

In embodiments of the disclosed device, the nipple extension 8 has on its outside diameter a spiral air channel 20 which may be similar in appearance to an external acme thread. This may give the nipple extension 8 an outside diameter greater than the outside diameter of the nipple extension 8 in other disclosed embodiments. A dip tube 3 having an inside diameter suitable for a snug fit onto the outside diameter of nipple extension 8 may be installed over the nipple until it bottoms against a tube stop feature 19 molded into the cap 2. The spiral air channel 20 may allow air to flow from the air volume 4 at the top of the bottle 1 to a point where it could intersperse with the liquid flow at the bottom of nipple extension 8. Therefore there may be no need for the core of the injection mold tooling that forms cap 2 to have some elements which are pulled straight off the part and other elements that are screw rotated off the part. The entire core of the injection mold tool may therefore be one piece when the helix pitch of the spiral air channel 20 matches the helix pitch of the threads 10 on the base of the cap 2.

An embodied method for operation of the disclosed high flow volume nasal irrigation device for alternating pulsatile and continuous fluid flow may be as follows. The bottle may be filled to a marked line with either previously prepared rinsing solution or with water (preferably comfortably warm). If filled with water the user may add a pre-packaged soluble mixture resulting in the desired solution when agitated. The user may screw the cap onto the bottle and align the dispensing orifice with one of his nostrils and lightly press the cap against the end of his nose to obtain a seal. With this connection made and while positioned over a sink or some suitable catch basin the user may squeeze the bottle to force the pulsatile flow into the nose and sinus cavities. Typically, when using the common fluid fill of 8 oz., best results are obtained with 3-4 squeezes applied to alternate nostrils, with the nose being blown between squeezes. Air at the top of the bottle may need to be replenished at intervals unless accommodations are made for a significantly large volume of air at the top of the bottle (which is unnecessary, since the cleansing action is best when used as described above). Once the contents have been expended the bottle will need to be rinsed and stored in a manner that favors drying and reduces the possibility of contamination.

In addition to the previously disclosed advantages of low cost pulsatile flow leading to improved cleaning action, an air bleed is open between the air volume at the top of the bottle and the atmosphere through the air channel in the cap, the air metering orifice and the nipple orifice. Therefore, a full capped bottle may not inadvertently spill solution out the top when the bottle is picked up. The excess pressure created when the sides of the bottle are lightly squeezed is vented to the atmosphere. Also, it is common for conventional rinsing bottles to overflow after filling as the warm solution expands the air trapped in the top of the bottle by heating and humidifying the air. This does not happen with the disclosed device because the excess air pressure is bled to the atmosphere through the air channel in the cap, the air metering orifice and the nipple orifice.

What is claimed is:

1. A high flow volume nasal irrigation device, comprising:
  a) a squeeze bottle having an open end, a reservoir of a liquid and a volume of air, the squeeze bottle configured to elastically deform in response to a manual pressure from a user and thus pressurize the liquid and the air;
  b) a dip tube configured to convey a pressurized liquid flow from a first end inside the squeeze bottle to a second end outside the squeeze bottle, the second end comprising a void in a tube wall;
  c) a removable nipple cap disposed on the squeeze bottle open end, the removable nipple cap comprising a nipple orifice and a coaxially aligned cap socket configured to rotatably seal with the dip tube second end to form a conduit with the dip tube; and
  d) an air channel formed axially and adjacent to the cap socket, the air channel and the void configured to form an air metering orifice rotatably aligned to introduce a plurality of air pockets into the pressurized liquid flow from the volume of air and thus generate a pulsatile fluid flow.

2. The high flow volume nasal irrigation device of claim 1, wherein the void comprises a bevel extending from adjacent a central radial axis of the dip tube at the second end proximally at an acute angle to an outer perimeter of the dip tube wall.

3. The high flow volume nasal irrigation device of claim 1, wherein the void comprises a gap, a notch, a bevel or any other void in the tube wall.

4. The high flow volume nasal irrigation device of claim 1, wherein a cross sectional inside area of the air metering orifice is variable in relation to an alignment of the dip tube void with the air channel a nominal 1.2 mm$^2$ (0.002 inches$^2$), to a maximum cross sectional inside area of 2.5 mm$^2$ (0.004 inches$^2$) and to a minimum cross sectional inside area of zero in the event the void is unaligned with the air channel and air flow is shut off to the pressurized liquid flow.

5. The high flow volume nasal irrigation device of claim 1, wherein a variable alignment of the dip tube second end void and the air channel produce a variable size and a variable length of air pockets introduced into the pressurized liquid flow and a non-alignment of the void and the air channel produces a continuous liquid flow at the nipple orifice.

6. The high flow volume nasal irrigation device of claim 1, wherein the squeeze bottle comprises a circumferential line and one or more indicia placed externally on the squeeze bottle to indicate a minimum liquid to air ratio to produce the pulsatile fluid flow in the dip tube for a first squeeze of the bottle by the user.

* * * * *